United States Patent [19]

Kauffman

[11] 4,113,945

[45] Sep. 12, 1978

[54] NOVEL CATALYST SYSTEM FOR TRIMERIZATION OF ORGANIC ISOCYANATES

[75] Inventor: William J. Kauffman, Lancaster, Pa.

[73] Assignee: Armstrong Cork Company, Lancaster, Pa.

[21] Appl. No.: 812,342

[22] Filed: Jul. 1, 1977

Related U.S. Application Data

[60] Continuation-in-part of Ser. No. 750,246, Dec. 13, 1976, abandoned, which is a division of Ser. No. 670,881, Mar. 26, 1976, Pat. No. 4,025,469.

[51] Int. Cl.$^2$ .............................................. C07D 273/04
[52] U.S. Cl. ........................................ 544/67; 544/69; 544/193; 544/221
[58] Field of Search ...................................... 544/67, 69

[56] References Cited

U.S. PATENT DOCUMENTS

| 3,527,657 | 9/1970 | Huther et al. ..................... 117/138.8 |
| 4,025,469 | 5/1977 | Kauffman ..................... 260/2.5 AW |

OTHER PUBLICATIONS

Von Hans Krassig, Makromol. Chem. vol. 17, pp. 77 to 130 (1956) (Brief English abst. in Chem. Abst. vol., cols. 13953–13954 (1956).

Bergmann et al., Ber. Deut. Chem. vol. 57, pp. 662–664 (1924) (brief English abst. in Chem. Abst. vol. 18, p. 2683 (1924).

Walker (I), Formaldehyde, frontispage, pp. 199–202 and 209–210, Reinhold Publ. Corp. NY (1944).

Walker (II), Formaldehyde, frontispage and p. 282 (1953), Reinhold Publ. Corp. NY.

*Primary Examiner*—John D. Randolph

[57] ABSTRACT

A novel catalyst system is described that is useful in the trimerization of organic isocyanates. The system comprises (1) N,N',N"-trisdialkylaminoalkyl-s-hexahydrotriazine and (2) a compound selected from the group consisting of 3,5-bis(N,N-dialkylaminoalkyl)-1,3,5-tetrahydrooxadiazine, 5-(N,N-dialkylaminoalkyl)-1,3,5-dihydrodioxazine and the mixtures thereof.

1 Claim, No Drawings

NOVEL CATALYST SYSTEM FOR TRIMERIZATION OF ORGANIC ISOCYANATES

This is a continuation-in-part of U.S. patent application Ser. No. 750,246, filed Dec. 13, 1976, now abandoned, which is a division of U.S. patent application Ser. No. 670,881, filed Mar. 26, 1976, now U.S. Pat. No. 4,025,469.

BACKGROUND OF THE INVENTION

1. Field of the Invention

This invention relates to an improved process for the trimerization of organic isocyanates. More particularly, it is concerned with the process for the preparation of isocyanurates, polyisocyanurates and cellular foams characterized by isocyanurate linkages.

2. Description of the Prior Art

The prior art methods for the trimerization of organic isocyanates have been disclosed in U.S. Pat. No. 2,993,870 which teaches the use of certain catalytic hexahydrotriazine compounds to facilitate the cyclization reaction. Varied density polyisocyanurate foam articles have also been described as being produced using polyisocyanates and certain hexahydrotriazine catalysts; see for example U.S. Pat. Nos. 3,644,168 and 3,836,427. While these disclosures provide examples of catalysts that are effective in the isocyanate/isocyanurate systems, the activity of the catalysts does not permit facile control of the trimerization reaction. For example, it is well known that small changes in concentrations of these catalysts, within certain concentration ranges exhibit enormous changes in the rate of reaction of the isocyanate group. Further, to effect a sufficiently rapid and economical reaction rate, relatively large quantities of the expensive hexahydrotriazines are necessary. It has heretofore been believed that only substituted triazines could function as useful catalysts for the cyclization/condensation reaction of isocyanates to isocyanurates, thus limiting the selection of useful catalysts.

The present invention is based on the discovery that nitrogen-containing heteocyclic amines other than the prior art hexahydrotriazines are useful in the preparation of isocyanurates and cellular, as well as non-cellular, isocyanurate-containing polymers.

As a further embodiment of the present invention, the method of preparation for these catalytic nitrogen-containing heterocyclic amines is also disclosed. The synthesis of these heterocyclic materials, e.g., the dihydrodioxazines have been revealed in the early prior art as being effected by treating a primary amine with excess formaldehyde. See U.S. Pat. No. 3,527,657. While it was recognized that the products of the reaction are controlled by adjusting the ratios of reactant, i.e., large excesses of formaldehyde result in dioxazines while equimolar reactions yield hexahydrotriazines, the fact that the formation of the triazine, dioxazine, and even the oxadiazine can be readily controlled by adjusting the temperature at which the reaction occurs has not been discovered, and see J. F. Walker Formaldehyde, Reinhold Publishing Corp., 1976, 360 ff.

SUMMARY OF THE INVENTION

It is the primary object of this invention to provide a method for the preparation of isocyanurates and isocyanurate-containing polymers by the cyclization/condensation reaction of an organic isocyanate or polyisocyanate in the presence of a catalytically sufficient amount of a novel catalyst system comprising a triazene of the formula:

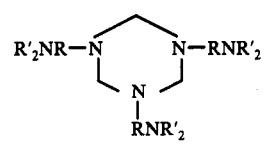

wherein each R individually is alkylene such as ethylene, propylene, butylene and the like, and R' is lower alkyl such as methyl, ethyl, propyl, isopropyl, butyl, isobutyl, t-butyl, pentyl and the like, and mixtures thereof, and a compound selected from the group consisting of oxadiazine of the formula:

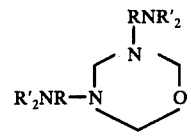

wherein R and R' are the same as disclosed above, dioxazine of the formula:

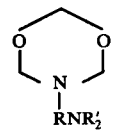

wherein R and R' are the same as described above, and mixtures thereof.

It is a further object of the present invention to provide a method for the preparation of the above disclosed alkyl-substituted oxadiazines and dioxazines.

This and other various objects and advantages of the present invention will become apparent by reference to the following detailed description and examples thereof.

DESCRIPTION OF THE PREFERRED EMBODIMENTS

A. The Catalyst System

The substituted triazenes useful as one of the components in the catalyst system of the present invention are generally structurally designated as:

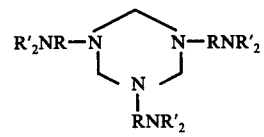

wherein each R individually is alkylene such as ethylene, propylene, butylene, and the like, and R' is lower alkyl such as methyl, ethyl, propyl, isopropyl, butyl, isobutyl, t-butyl, pentyl, and the like, and mixtures thereof. The 1,3,5-tris(N,N-dialkylaminoalkyl)-s-hexahydrotriazines are generally prepared by reacting a dialkylaminoalkylamine and a 37% aqueous solution of formaldehyde (e.g., formalin) at a temperature of from about 10° to about 100° C. and atmospheric pressure. The amine and formalin are mixed together with stirring and the temperature of the resulting reaction medium is then raised to the desired temperature. After separation by the addition of a strong base such as potassium hydroxide to the reaction solution, the hexahydrotriazine is removed from the reaction mixture and purified by distillation if desired. These hexahydrotriazines and their method of preparation are more particularly described by Nicholas et al, J. Cellular Plastics, 1(1), 85 (1965) and Greymore, J. Chem. Soc. 1943 (1931). Representative of the 1,3,5-tris(N,N-dialkylaminoalkyl)-s-hexahydrotriazines useful herein include, for example, 1,3,5-tris(N,N-dimethyl-2-aminoethyl)-s-hexahydrotriazine; 1,3,5-tris(N,N-dimethyl- 2-aminopropyl)-s-hexahydrotriazine; and the like; 1,3,5-tris(N,N-diethyl-2-aminoethyl)-s-hexahydrotriazine; 1,3,5-tris(N,N-diethyl-3-aminopropyl)-s-hexahydrotriazine; and the like; 1,3,5-tris(N,N-dipropyl-2-aminoethyl)-s-hexahydrotriazine; and the like; and so forth. The preferred compound is 1,3,5-tris(N,N-dimethyl-3-aminopropyl)-s-hexahydrotriazine which can also be designated as 1,3,5-tris(3-dimethylaminopropyl)-s-hexahydrotriazine.

As to the other essential parts of the co-catalyst system of the present invention, 3,5-bis(N,N-dialkylaminoalkyl)-1,3,5-tetrahydrooxadiazine.

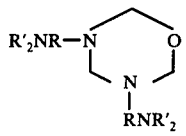

5-(N,N-dialkylaminoalkyl)-1,3,5-dihydrodioxazine

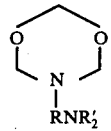

where R and R' are the same as described before, or mixtures thereof are also employed. The oxadiazines and dioxazines of this invention are generally prepared by the reaction of dialkylamino alkylamine with excess 37% aqueous solution of formaldehyde, e.g., formalin, at a temperature of about 35° to about 50° C. and about 0° to about 35° C. respectively, and atmospheric pressure.

B. The Reactants

The present invention provides a method for the trimerization of organic isocyanates by the catalytically-induced cyclization of the isocyanate group according to the following equation:

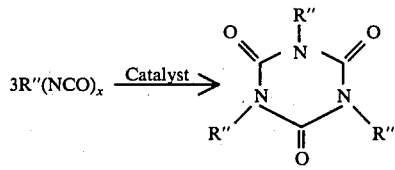

in which R"NCO is an organic isocyanate and the product of the reaction, an isocyanurate, is formed by the trimerization sometimes termed herein as cyclization/condensation of the isocyanate groups and believed to have the formula given in the above equation.

The organic isocyanates which are advantageously employed in the present invention and represented in the above formula, generally have the formula as shown below:

where R is a mono or polyisocyanate organic radical selected from the group of aliphatic, aromatic, or alkyl substituted aromatic, as well as mixtures thereof, and $x$ is an integer corresponding to the valence number of R" and being at least 1. It should be noted that when $x$ is greater than 1, polymeric materials are formed, such being characterized by isocyanurate linkages. Representative of the organic monoisocyanates contemplated herein include, for example, alkyl, such as butyl and pentyl; aryl, such as phenyl and tolyl; aralkyl, such as benzyl; and mixtures thereof and the like. Those organic polyisocyanates contemplated in the method of this invention include, for example, aromatic diisocyanates such as 2,4-toluene diisocyanate, 2,6-toluene diisocyanate, and mixtures thereof, methylene diphenyl diisocyanate; aromatic tetraisocyanates; alkylaryl polyisocyanates such as xylylene diisocyanate; aliphatic polyisocyanates such as lysine diisocyanate dimethylester and the like; and mixtures thereof.

The aforementioned mono and polyisocyanates may be prepared by any of the conventional methods known in the prior art such as the phosgenation of the corresponding primary organic amine.

Still other organic polyisocyanates contemplated by the present invention are those prepolymers prepared by reacting an excess of organic polyisocyanate or mixtures thereof with a minor amount of an active hydrogen-containing compound. These compounds, as well as their method of preparation and chemical and physical properties are well known in the art. The use of any one specific active hydrogen-containing compound is not critical hereto, rather, any such compound that can be used to prepare such prepolymers can be employed herein. One general technique for such preparation is by the reaction of an organic polyisocyanate with less than the stoichiometric amount of the active hydrogen-containing compound based on the weight of the polyisocyanate. Suitable groups of the active hydrogen-containing compounds include —OH, —NH—, —COOH, and —SH. Specific examples of those organic compounds containing at least two active hydrogen-containing groups which are reactive with an isocyanate group are hydroxyl-terminated polyesters, polyalkylene ether polyols, hydroxyl-terminated polyurethane polymers, polyhydric polythioethers, alkylene oxide adducts of phosphorus-containing acids, polyacetals, aliphatic polyols, aliphatic thiols including alkane, alkene and alkyne thiols having two or more —SH groups; and diamines including both aromatic, aliphatic and heterocyclic diamines, as well as mixtures thereof. Compounds which contain two or more different groups within the above-defined classes may also be used in accordance with the process of the present invention such as, for example, amino alcohols which contain an amino group and a hydroxyl group. Also, compounds may be used which contain one —SH group and one —OH group as well as those which contain an amino group and a —SH group.

Any suitable hydroxyl-terminated polyester may be used such as are obtained, for example, from polycarboxylic acids and polyhydric alcohols. Any suitable polycarboxylic acid may be used such as oxalic acid, malonic acid, succinic acid, glutaric acid, adipic acid, pimelic acid, suberic acid, azelaic acid, sebacic acid, brassylic acid, thapsic acid, maleic acid, fumaric acid, glutaconic acid, -hydromuconic acid, -hydromuconic acid, -butyl- -ethyl-glutaric acid, -diethylsuccinic acid, isophthalic acid, terephthalic acid, hemimellitic acid, and 1,4-cyclohexane-dicarboxylic acid. Any suitable polyhydric alcohol, including both aliphatic and aromatic polyhydric alcohols may be used such as ethylene glycol, 1,3-propylene glycol, 1,2-propylene glycol, 1,4-butylene glycol, 1,3-butylene glycol, 1,2-butylene glycol, 1,5-pentanediol, 1,4-pentanediol, 1,3-pentanediol, 1,6-hexanediol, 1,7-heptanediol, glycerol, 1,1,1-trimethylolpropane, 1,1,1-trimethylolethane, hexane-1,2,6-trio, -methyl glucoside, pentaerythritol, and sorbitol. Also included within the term "polyhydric alcohol" are compounds derived from phenol such as 2,2-(4,4'-hydroxyphenol)propane, commonly known as Bisphenol A.

Any suitable polyalkylene ether polyol may be used such as the polymerization product of an alkylene oxide or of an alkylene oxide with a polyhydric alcohol. In this respect, any suitable polyhydric alcohol may be used such as disclosed above for the use of the preparation of the hydroxyl-terminated polyesters. Any suitable alkylene oxide may be used such as ethylene oxide, propylene oxide, butylene oxide, amylene oxide, and heteric or block copolymers of these oxides. The polyalkylene polyether polyols may be prepared from other starting materials such as tetrahydrofuran and alkylene oxide-tetrahydrofuran copolymers; epihalohydrins such as epichlorohydrin; as well as aralkylene oxides such as styrene oxide. The polyalkylene polyether polyols may have either primary or secondary hydroxyl groups and preferably, are polyethers prepared from alkylene oxides having from two to six carbon atoms such as polyethylene ether glycols, polypropylene ether glycols, and polybutylene ether glycols. The polyalkylene polyether polyols may be prepared by any known process such as, for example, the process disclosed by Wurtz in 1859 and Encyclopedia of Chemical Technology, Vol. 7, pp. 257-262, published by Interscience Publishers, Inc. (1951) or in U.S. Pat. No. 1,922,459.

Any suitable polyhydric polythioether may be used such as, for example, the condensation product of thiodigylcol or the reaction product of a dihydric alcohol such as is disclosed above for the preparation of the hydroxyl-terminated polyesters with any other suitable thioether glycol.

The hydroxyl-terminated polyester may also be a polyester amide such as is obtained by including some amine or amino alcohol as a reactant for the preparation of the polyesters. Thus, polyester amides may be obtained by condensing an amino alcohol such as ethanolamine with the polycarboxylic acids set forth above, or they may be made using the same components that make up the hydroxyl-terminated polyester with only a portion of the components being a diamine such as ethylene diamine.

Alkylene oxide adducts of acids of phosphorus which may be used include those neutral adducts prepared from the alkylene oxides disclosed above for use in the preparation of polyalkylene polyether polyols. Acids of phosphorus which may be used are acids having a $P_2O_5$ equivalency of from about 72% to about 95%. The phosphoric acids are preferred.

Any suitable hydroxyl-terminated polyacetal may be used such as, for example, the reaction product of formaldehyde or other suitable aldehyde with a dihydric alcohol or an alkylene oxide such as those disclosed above.

Any suitable aliphatic thiol including alkane thiols containing at least two —SH groups may be used such as 1,2-ethanedithiol, 1,2-propanedithiol, 1,3-propanedithiol, and 1,6-hexanedithiol; alkenethiols such as 2-butene-1,4-dithiol; and alkynethiols such as 3-hexyne-1,6-dithiol.

Any suitable polyamine may be used including aromatic polyamines such as p-aminoaniline, 1,5-diaminonaphthlene, and 2,4-diaminotoluene; aliphatic polyamines such as ethylenediamine, 1,3-propylenediamine, 1,4-butylenediamine, and 1,3-butylenediamine, as well as substituted secondary derivatives thereof.

In the practice of the present invention, the preferred organic polyisocyanate is either crude toluene diisocyanate, toluene diisocyanate, methylene diphenyl diisocyanate, crude methylene diphenyl diisocyanate, or mixtures thereof.

The novel co-catalyst system of the present invention can also be used in a process for the synthesis of cellular foams characterized by a majority of isocyanurate linkages. According to this aspect of the present invention, a gas-generating reaction or agent may by admixed with the aforementioned polyisocyanates to effect the rigid cellular foam.

The gas-generating agent used to form the above-mentioned rigid foam may be water or it may be an inert liquid of low boiling point which vaporizes under the influence of the exothermic polyisocyanurate-forming reaction. It is often advantageous to use both types of gas-generating agents in conjunction with one another.

When water is used as the gas-generating agent, it is usually present in an amount from 1% to 10% by weight of the polyisocyanate. The amount of water preferred as a gas-generating agent is from 1% to 5% by weight of polyisocyanate.

Suitable low-boiling liquids are those that are inert toward the foam-forming reactants or products and have boiling points not exceeding 75° C. at atmospheric pressure and preferably between −40° C. and 50° C. Examples of such liquids are the halogenated hydrocarbons such as methylene chloride, vinylidene chloride, trichloromethane, dichlorodifluoromethane, dichloromonofluoromethane, monochlorodifluoromethane, dichlorotetrafluoromethane, 1,1,2-trichloro-1,2,2-trifluoroethane, dibromodifluoromethane and monobromotrifluoroethane. Mixtures of these low-boiling liquids with each other and/or with other substituted or unsubstituted hydrocarbons may also be used. Such liquids are usually employed in amounts of from 1% to 100% preferably between 5% and 50% by weight of the polyisocyanate reactant.

Solid gas-generating materials may also be employed in the formation of a cellular foam characterized by a majority of isocyanurate linkages. Suitable gas-generating solids of this type are those that decompose to partially or totally gaseous components at temperatures of 40° to 200° C. Examples of such are ammonium carbamoyl sulfonate and azobisformamide. These materials are usually employed in amounts of 1% to 40%, but preferably between 1% to 20% by weight.

In another embodiment of this invention, cellular foams having a majority of isocyanurate linkages may also be prepared from the novel co-catalyst system and those prepolymeric polyisocyanates described above by causing the reactants to be mixed at the reaction initiating temperature of from 100° to 150° C. Under such conditions, carbon dioxide is generated and foam formation begins without the addition of external gas-generating materials. Alternately, these foams may be prepared by adding the catalyst to the prepolyisocyanate and when necessary, heating the mixture to the initiation temperature or separately preheating the polyisocyanate and catalyst system and then mixing the two together.

The physical character of the foam can be altered from that of a rigid one to those foams having elastomeric character (semi-rigid) merely by adjusting the amount of polyol present in the prepolymeric isocyanate. Thus, when maximum elastomeric character is desired, a slight excess of organic polyisocyanate is combined with the polyol to yield a polyisocyanate terminated prepolymer having urethane linkages. However, when rigid foams are desired, all polyol may be excluded and the organic polyisocyanate allowed to self-polymerize to an essentially polyisocyanurate foam. Of course, any combination between these two extremes may be employed.

The present invention also contemplates the incorporation of additional ingredients in the foam formulation to tailor the properties thereof. Thus, plasticizers, such as tris(2-chloroethyl)phosphate; surfactants, such as the silicone surfactants, e.g., alkylpolysiloxanes and polyalkylsiloxanes; active hydrogen-containing compounds, such as those described above for preparing the prepolymers may be employed in this invention. Also, inorganic fillers, pigments and the like may also be used.

The foam formulations also may benefit from the presence of any of the well-known urethane promoting catalysts in systems where the active hydrogen-containing compound (e.g. the polyol) and polyisocyanate are admixed. These catalysts include dibutylin dilaurate, trimethylene diamine, stannous octoate, and the like.

In preparing the foams with the additional ingredients and, in particular, with halohydrocarbon blowing agents, plasticizers and surfactants, it is preferred to facilitate handling that the halohydrocarbon be dissolved in the polyisocyanate prior to commencing reaction and the plasticizers and surfactants be preblended with the catalyst system. It should be pointed out that in many instances, the catalyst system is a solid at ambient conditions. Thus, it can be first dissolved in an inert solvent therefor, such as a plasticizer, a surfactant or blowing agent, thereby providing an easy means for introducing both ingredients into the system. In any event, the foams prepared in accordance herewith are cellular products having a density of from about 1 to 20 pounds per cubic foot which, because of the isocyanurate linkage, exhibit excellent flame properties such as thermal stability, fire resistance, low smoke evolution and excellent weight retention under high temperature conditions.

In preparing the isocyanurates of this invention in the presence of the catalyst system, generally from about 1 part to 10 parts by weight of catalyst system per 100 parts by weight of organic isocyanate or polyisocyanate are employed. Preferably from about 1 part to 5 parts by weight of catalyst per 100 parts of organic isocyanate is employed. Most preferred is 3 parts of catalyst to per 100 parts by weight of organic isocyanate or polyisocyanate.

The catalyst system of this invention is prepared in a weight ratio of hexahydrotriazine:tetrahydrooxadiazine:dihydrodioxazine of 1:10:10 to 10:1:0. Preferably from about 3:2:0 to 2:3:3 of the hexahydrotriazine:- tetrahydrooxadiazine:dihydrodioxazine is employed. However, catalyst systems of hexahydrotriazine:dihydrodioxazine of 1:10 to 10:1 are also useful for this invention.

It is most preferred, however, to employ as the catalyst system of this invention the ratio of hexahydrotriazine:tetrahydrooxadiazine 1:1.

In addition to the heretofore described utility, the co-catalyst systems of this invention are also useful as carbodiimide foam-forming catalyst and the like.

For a more complete understanding of the present invention, the following examples describe the manner and process of making and using the components of this invention and set forth the best mode contemplated by the inventors for carrying out the objects of their invention. They are not to construed as limiting this invention in any way.

EXAMPLE 1

This example illustrates the preparation of a tetrahydrooxadiazine adduct in accordance with the present invention.

3,5-Bis(N,N-dimethylaminopropyl)-1,3,5-tetrahydrooxadiazine

Dimethylaminopropylamine (102 g., 1.0 mole) was added dropwise with stirring to a 37% solution of aqueous formaldehyde (125 g., 1.5 moles) such that the temperature was about 35° C. but did not exceed 50°. The addition required 1.5 hours after which the reaction mixture was allowed to stand for an additional 1.5 hours. The solution was then cooled in an ice bath and a total of 40 g. of potassium hydroxide was added such that the temperature did not exceed 25°. The organic layer was separated and subjected to vacuum distillation resulting in the isolation of the above-disclosed tetrahydro-oxadiazine (77.5 g., 0.3 mole), b.p. 100°–110°/0.01 mm.

Anal. Calcd. for $C_{13}H_{30}N_4O$: C, 60.43; H, 11.70; N, 21.68, molecular weight 258.4. Found: C, 60.26; H, 11.90; N, 21.80; molecular weight 270.

EXAMPLE 2

This example illustrates the preparation of a hexahydrotriazine.

N,N',N''-Tris(dimethylaminopropyl)hexahydro-s-triazine

To a stirred solution of 37% aqueous formaldehyde (115 g., 1.42 moles) was added N,N-dimethylaminopropylamine (150 g., 1.47 moles) at a rate to keep the temperature between 50°–55°. The addition was complete after 3 hours and the reaction stirred for an additional hour. The reaction mixture was then cooled in an ice bath and potassium hydroxide (115 g.) added such that the temperature did not exceed 25°. The organic layer was separated and subjected to vacuum distillation resulting in the isolation of N,N',N''-tris(dimethylaminopropyl)hexahydro-s-triazine (140 g., 0.41 mole), b.p. 135°–140°/0.01 mm.

Anal. Calcd. for $C_{18}H_{42}N_6$: C, 63.11; H, 12.36; N, 24.53; molecular weight 342.6. Found: C, 63.35; H, 12.27; N, 24.33; molecular weight 347.

EXAMPLE 3

This example illustrates the preparation of dihydrodioxazine.

5-N,N-Dimethylaminopropyl-1,3,5-dihydro-dioxazine

Dimethylaminopropylamine (20.4 g. 0.2 mole) was added dropwise to a 37% aqueous formaldehyde solution (80 g., 0.98 mole) over a period of one hour. The temperature of the reaction was about 0° C. but did not exceed 35° C. during this addition. The reaction was then cooled in an ice bath and 80 g. of potassium hydroxide added such that the temperature did not exceed 25° C. The organic layer was separated and subjected to vacuum distillation and the above disclosed dioxazine was isolated (6.5 g., 0.04 mole), b.p. 45°/.01 mm.

Anal. Calcd. for $C_8H_{18}N_2O_2$: C, 55.15; H, 10.41; N, 16.08; molecular weight, 174. Found: C, 55.15; H, 10.48; N, 16.04; molecular weight 175.

EXAMPLE 4

General Procedure for Determination of Catalyst Activity — Trimerization of Organic Isocyanate Phenylisocyanate (10 g.) was dissolved in 25 ml of o-dichlorobenzene and added to a dewar flask equipped with a thermocouple temperature sensor and a small magnetic stirrer. A 5 ml aliquot of a o-dichlorobenzene solution containing 0.1 gram of a catalyst system comprising a 50:50 mixture of 3,5-bis(N,N-dimethylaminopropyl)-1,3,5-tetrahydro-oxadiazine and N,N',N''-tris(dimethylaminopropyl)hexahydro-s-triazine was then carefully added and the time of reaction, as indicated by the reaction exotherm monitored by the thermocouple, was recorded. Stirring was continued for one hour after the maximum in the exotherm was observed. The solid precipitant was collected by filtration. Triphenylisocyanurate (m.p. 268°-270° C., 90% yield) was obtained as a result and characterized by mixed melting point, IR, NMR and chemical analyses.

EXAMPLE 5

Similar reactions were carried out to illustrate the reactivity enhancement of the various catalyst systems of this invention. The table below sets forth the catalytic compositions used to prepare triphenylisocyanurate in the manner shown above (Example 4), the time to the mid-point of exothermic response, and the relative rate of generation of the exotherm (dT/dt) normalized to the rate obtained for N,N',N''-tris-dimethylaminopropyl-s-hexahydro triazine (HHT).

Table 1

| Experimental Designation | Cyclic Tertiary Amine Catalyst System | | | | |
|---|---|---|---|---|---|
| | HHT[1](g) | 2[2](g) | 3[3](g) | $T_i$ | Rr |
| C-1 | 0.05 | 0.05 | — | 13 | 1 |
| C-2 | 0.033 | 0.67 | — | 28 | 1 |
| C-3 | 0.025 | 0.075 | — | 50 | .8 |
| C-4 | 0.017 | 0.083 | — | 55 | .7 |
| C-8 | — | 0.2 | — | 60 | .5 |
| C-10 | — | 0.1 | — | — | — |
| D-1 | 0.05 | 0.05 | 0.01 | 15 | 1 |
| D-2 | 0.017 | 0.083 | 0.01 | 55 | .7 |
| D-4 | 0.05 | — | 0.05 | 25 | 1 |

[1]N,N',N''-tri-dimethylaminopropyl-s-hexahydro triazine
[2]3,5-bis(N,N-dimethylaminopropyl)-1,3,5-tetrahydro oxadiazine
[3]5-(N,N-dimethylaminopropyl)-1,3,5-dihydrodioxazine Table II

| Experimental Designation | Cyclic Tertiary Amine Catalyst System[1] | | | | |
|---|---|---|---|---|---|
| | HHT | 2 | 3 | $T_i$ | Rr |
| A-2 | .025 | — | — | — | — |
| A-1 | .05 | — | — | 25 | 1 |
| A | 0.1 | — | — | 10 | 1 |

Table II-continued

| Experimental Designation | Cyclic Tertiary Amine Catalyst System[1] | | | | |
|---|---|---|---|---|---|
| | HHT | 2 | 3 | $T_i$ | Rr |
| 2A | 0.2 | — | — | 5 | 1 |

[1]N,N',N''-tri-dimethylaminopropyl-s-hexahydro triazine
[2]HHT, 2 and 3 are the same as set forth in Table I.

EXAMPLE 6

Preparation of Semi Rigid Isocyanurate Foam

The following formulation was employed using a "one shot" foaming technique to produce a semi-rigid isocyanurate foam. The resultant foam was post cured for 10 minutes at 80° C.

| Ingredients[a] | Parts by Weight |
|---|---|
| Polyol - Multranol 7100 | 31.7 |
| Surfactant - Tegastab 33640 | 0.8 |
| Stannous Octoate | 0.2 |
| Trimerization Catalyst: 60% 3,5-bis (dimethylaminopropyl)-1,3,5-tetrahydro oxadiazine; 40% HHT (see Table 1) | 1.0 |
| Blowing Agent - UCON 113 | 10.0 |
| Isocyanate - Upjohn Isonate 143-L | 40.0 |
| | NCO/OH = 1.0/0.1 |

[a]Multranol 7100, a product of Dow Chemical Company, having an OH # of 49 and an equivalent weight of 1145
Tegastab is a fire retardant silicon manufactured by Goldschmidt
UCON 113, a product of Union Carbide defined as a fluoro-carbon of b.p. 113° F.
Isonate 143-L, a product of Upjohn Company defined as a liquid methylene diphenyl diisocyanate The resultant foam had a density of 5.2 lb./ft.$^3$, excellent cell structure and was classified as semi-rigid using ASTM D-1056-68, and Mil.-R-6130B specifications.

EXAMPLE 7

Preparation of a Rigid Isocyanurate Foam

The following formulation was employed using a "one shot" foaming technique to produce a rigid isocyanurate foam. The resultant foam was post cured for 10 minutes at 80° C. before analyzing.

| Ingredients[b] | Parts by Weight |
|---|---|
| Polyol-multranol 7100 | 7.9 |
| Surfactant - Tegastab | 0.8 |
| Stannous Octoate | 0.2 |
| Trimerization Catalyst: Same as employed in semi-rigid formulation Example 6 | |
| Blowing agent - UCON 113 | 10.0 |
| Isocyanate - Upjohn Isonate 143-L | 40.0 |
| | NCO/OH = 1.0/0.025 |

[b]See Example 6

The resultant foam had a density of 4.4 lb./ft.$^3$, excellent cell structure and was classified as rigid using ASTM D-1056-68, and Mil-R-6130B specifications.

The following example summarizes in table form the various foams characterized by isocyanurate linkages and produced by utilizing the catalyst system of this invention.

EXAMPLE 8

| Polyol | Foam[c] | | | |
|---|---|---|---|---|
| | A | B | C | D |
| CP-3001 | 27.7 | 26.0 | 12.8 | — |
| Brominex 160P | 16.7 | — | — | — |
| Multranol 3900 | — | — | — | 106.3 |
| Dow (Silicon Surfactant) DC-201 | 1.0 | | | |
| G.E. (Silicon Surfactant) | | | | |

-continued

| Polyol | Foam | | | |
|---|---|---|---|---|
| | A | B | C | D |
| PFA-1200 | | | .6 | 1.5 |
| Tegastab (See Example 6) | — | .8 | — | — |
| Trimethylene diamine | .2 | .1 | .1 | .2 |
| Dibutyltin dilaurate | .2 | — | — | — |
| Stannous octoate | — | .1 | .1 | .2 |
| Trimellitic Anhydride | 20 | — | — | — |
| Catalyst system of this invention | .8 | .6 | .6 | .4 |
| Water | 1.7 | — | — | — |
| UCON-11B | — | 7 | 6 | 15 |
| UCON-113⁻ | | | | |
| PAPI-901 | 40 | — | — | — |
| Isonate 143-L (See Example 6) | — | 40 | 40 | 40 |
| NCO/OH | 1.05/0.10 | 1.05/0.05 | 1.05/0.25 | |

-continued

| Polyol | Foam | | | |
|---|---|---|---|---|
| | A | B | C | D |
| Density (lbs/ft³) | 3.2 | 2.9 | 2.6 | 6.2 |

ᶜAll components of these formulations are in parts by weight CP-3001 - a polyol of Dow Chemical Company of hydroxyl number 54.3-62.3
Brominex 160P, a bromine and phosphorous containing polyol of Swift & Company of hydroxyl number 46-50
Multranol 3900, a polyol diol of hydroxy number 54 and equivalent weight 1031
Catalyst system of this invention - this comprises 3,5-bis (dimethylaminopropyl)-1,3,5-tetrahydrodiazine:N,N',N''-tridimethylaminopropyl-s-hexahydrotriazine in 3:2
UCON 11B and 113 are fluorocarbon blowing agents of b.p. 76° and 113° F., respectively
PAPI-901, a polymeric isocyanate While the above describes the preferred embodiments of this invention, it will be understood that departures may be made therefrom within the scope of the specification and claims.

What is claimed is:
1. A compound of the formula:

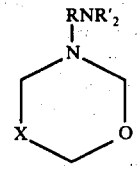

wherein X represents $N(RNR'_2)$, R represents a $C_2$ to $C_4$ alkylene group and R' represents a $C_1$ to $C_5$ alkyl group.

* * * * *